United States Patent
Davis et al.

(10) Patent No.: US 9,759,556 B2
(45) Date of Patent: Sep. 12, 2017

(54) ACOUSTIC PROBING TECHNIQUE FOR THE DETERMINATION OF INTERIOR PIPE COATING WEAR OR SCALE BUILD-UP AND LINER WEAR

(71) Applicant: CiDRA CORPORATE SERVICES INC., Wallingford, CT (US)

(72) Inventors: Michael A. Davis, Glastonbury, CT (US); Alan D. Kersey, South Glastonbury, CT (US); John Viega, Ellington, CT (US)

(73) Assignee: CiDRA Corporate Services, Inc., Wallingford, CT (US)

( * ) Notice: Subject to any disclaimer, the term of this patent is extended or adjusted under 35 U.S.C. 154(b) by 513 days.

(21) Appl. No.: 14/350,684

(22) PCT Filed: Oct. 18, 2012

(86) PCT No.: PCT/US2012/060811
§ 371 (c)(1),
(2) Date: Apr. 9, 2014

(87) PCT Pub. No.: WO2013/059458
PCT Pub. Date: Apr. 25, 2013

(65) Prior Publication Data
US 2014/0373631 A1   Dec. 25, 2014

Related U.S. Application Data

(60) Provisional application No. 61/548,513, filed on Oct. 18, 2011, provisional application No. 61/548,531, (Continued)

(51) Int. Cl.
| | |
|---|---|
| *G01N 29/04* | (2006.01) |
| *G01N 29/11* | (2006.01) |
| *G01N 29/44* | (2006.01) |
| *G01N 29/46* | (2006.01) |
| *G01B 17/02* | (2006.01) |
| *G01N 29/34* | (2006.01) |

(52) U.S. Cl.
CPC .......... *G01B 17/025* (2013.01); *G01N 29/04* (2013.01); *G01N 29/11* (2013.01); *G01N 29/348* (2013.01);
(Continued)

(58) Field of Classification Search
CPC .... G01B 17/025; G01N 29/04; G01N 29/348; G01N 29/44; G01N 2291/015;
(Continued)

(56) References Cited

U.S. PATENT DOCUMENTS

| | | |
|---|---|---|
| 4,328,707 A | 5/1982 | Clement et al. |
| 4,386,854 A | 6/1983 | Byer |

(Continued)

FOREIGN PATENT DOCUMENTS

| | | |
|---|---|---|
| WO | 2009114847 | 9/2009 |
| WO | 2011116264 | 9/2011 |

*Primary Examiner* — J M Saint Surin
(74) *Attorney, Agent, or Firm* — Ware, Fressola, Maguire & Barber LLP

(57) ABSTRACT

Apparatus is provided comprising a signal processor that receives signaling containing information about an acoustic signal swept and sensed over a frequency range in relation to a pipe; and determines information about the structure of the pipe based at least partly on two or more sub-frequency ranges that form part of the frequency range in the signaling received. The signal processor also receives the acoustic signal being transmitted to the pipe and corresponding signaling in the two or more sub-frequency ranges containing information about reflections of the acoustic signal back from the pipe; and determines information about the structure of the pipe based at least partly on a coherent mixing of the acoustic signal and the corresponding signaling in the two or more sub-frequency ranges using a coherent acoustic tomography technique. Alternatively, the signal processor also receives associated signaling in the two or more sub-frequency ranges containing information about associated resonance in a liner of a wall of the pipe and determines information about the liner of the wall of the pipe, based at least partly on the two or more sub-frequency ranges.

23 Claims, 3 Drawing Sheets

Related U.S. Application Data filed on Oct. 18, 2011, provisional application No. 61/555,746, filed on Nov. 4, 2011.

(52) U.S. Cl.
CPC ......... *G01N 29/44* (2013.01); *G01N 29/4454* (2013.01); *G01N 29/46* (2013.01); *G01N 2291/015* (2013.01); *G01N 2291/0237* (2013.01); *G01N 2291/0258* (2013.01); *G01N 2291/0289* (2013.01); *G01N 2291/042* (2013.01)

(58) Field of Classification Search
CPC ... G01N 2291/0237; G01N 2291/0289; G01N 2291/042
USPC .......................................................... 73/627
See application file for complete search history.

(56) References Cited

U.S. PATENT DOCUMENTS

| | | |
|---|---|---|
| 4,539,847 A | 9/1985 | Paap |
| 5,181,778 A | 1/1993 | Beller |
| 6,078,397 A | 6/2000 | Monchalin et al. |
| 2004/0099815 A1 | 5/2004 | Sfez et al. |
| 2008/0260324 A1 | 10/2008 | Takahashi |
| 2009/0078049 A1 | 3/2009 | Sinha |
| 2009/0133501 A1 | 5/2009 | Georgeson |
| 2010/0078090 A1 | 4/2010 | Miller et al. |

Apparatus 10

Signal processor 10a configured to receive signaling containing information about acoustic signals swept and sensed over a frequency range in relation to a pipe; and determine information about the structure of the pipe based at least partly on two or more sub-frequency ranges that forms part of the frequency range in the signaling received.

Other modules 10b for implementing the signal processing functionality, including a memory module, busing architecture and input/output Modules.

Figure 1

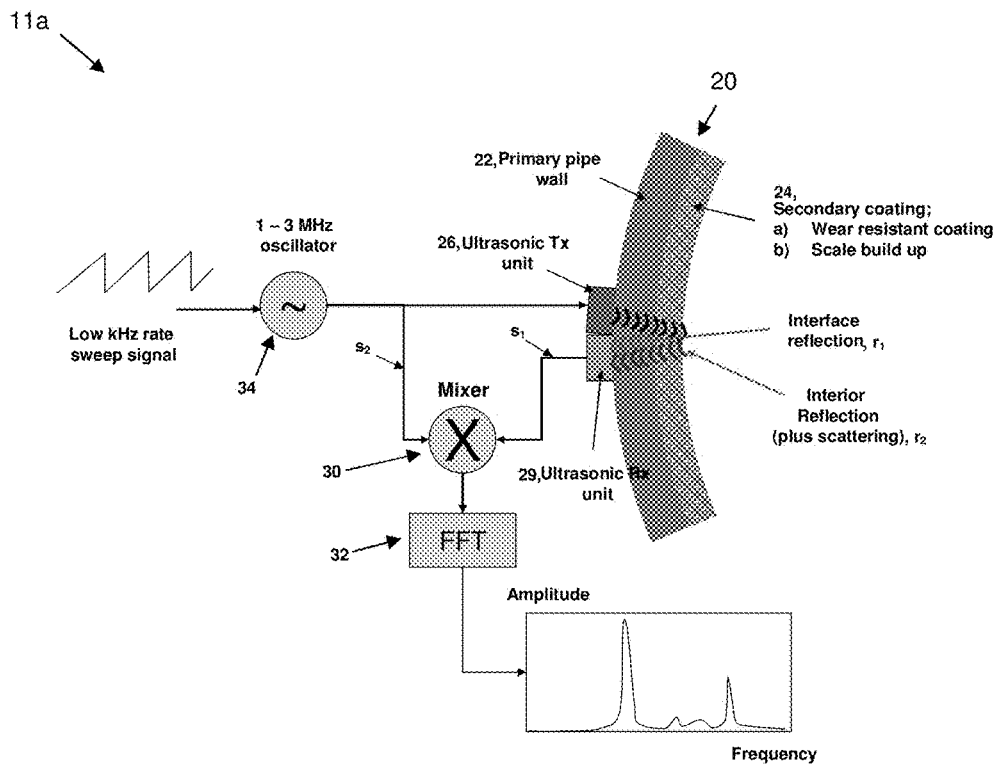
Figure 2: Pipe & Coating Thickness Monitoring Using Coherent Acoustic Tomography
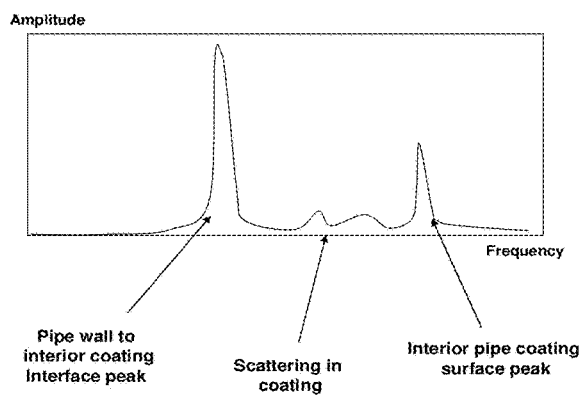
Figure 3: Frequency Transfer Function Representation of Pipe-Wall Boundaries Due to Acoustic Scattering and Reflection

Acoustic Probing Technique for the determination of Pipe Liner wear

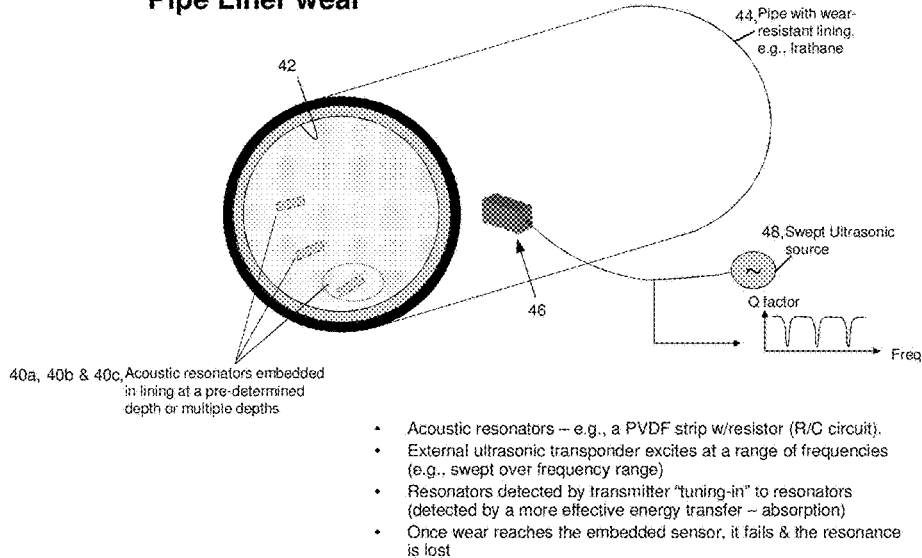

- Acoustic resonators – e.g., a PVDF strip w/resistor (R/C circuit).
- External ultrasonic transponder excites at a range of frequencies (e.g., swept over frequency range)
- Resonators detected by transmitter "tuning-in" to resonators (detected by a more effective energy transfer – absorption)
- Once wear reaches the embedded sensor, it fails & the resonance is lost

Figure 4: Concept

Principle of Operation

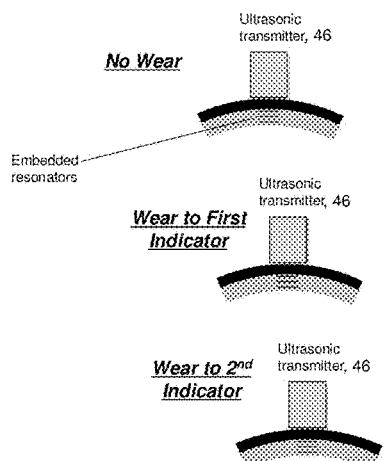

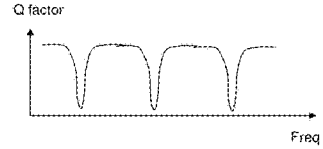

Figure 5a

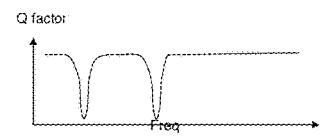

Figure 5b

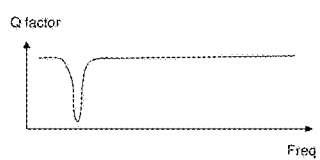

Figure 5c

Figure 5: Principle of Operation

ACOUSTIC PROBING TECHNIQUE FOR THE DETERMINATION OF INTERIOR PIPE COATING WEAR OR SCALE BUILD-UP AND LINER WEAR

CROSS-REFERENCE TO RELATED APPLICATIONS

This application corresponds to international patent application serial no. PCT/US2012/060811, filed 18 Oct. 2012, which claims benefit to provisional patent application Ser. No. 61/548,513, filed 18 Oct. 2011; patent application Ser. No. 61/548,531, filed 18 Oct. 2011, patent application Ser. No. 61/555,746, filed 4 Nov. 2011.

BACKGROUND OF THE INVENTION

1. Field of Invention

This invention relates to an acoustic probing technique for wear mitigation in a pipe, a pipeline or a liner of a pipe; and more particularly relates to a method and apparatus for determining coating wear or scale build-up and liner wear.

2. Description of Related Art

In a range of industrial applications, it can be important to assess the build up of an undesired coating, or the wear of an intentionally incorporated coating/liner on the inside of a process pipe line. For example:

1) In many processes scale deposits can build up on the interior of a pipe, and it is important to monitor this build up as these deposits can have detrimental effects on the throughput and performance of the process. Uncontrolled scale build up will typically result in a complete blockage of the pipe. Examples include areas such as pulp and paper processing plants, petro-chemical plants, and oil and gas distribution pipelines.

2) In many slurry and chemically aggressive applications, pipes are often coated with a liner to protect the inner pipe wall from corrosion and or erosion due to the flowing fluids, and knowledge of the thickness of these liners is important to ensure the integrity of the process-pipe or pipeline structure: As an example, to overcome the significant wear that can occur in pipelines carrying slurry materials such as in the oil sands industry, many suppliers are adopting pipes lined with materials, such as hard abrasion resistant materials such as chromium, or softer compliant elastomers such as urethanes.

In both sets of examples given above, monitoring of the coating or liner on the inside of a pipe wall is important for the integrity of the process system.

Ultrasonic non-destructive examination (NDE) approaches to detecting the thickness of a pipe wall are widely and successfully used in across industrial applications. By way of example, NDE sensors may be designed and configured to measure the pipe-wall thickness, e.g., including known techniques and monitoring devices provided in the marketplace in conjunction with the trademark HALO® system by the assignee of the instant patent application, can be used to monitor the performance of a so-called "sacrificial" coating and ensure that the steel wall is not being abraded significantly. By way of example, see the NDE techniques disclosed in PCT application No. PCT/US11/28957, filed 18 Mar. 2011, entitled "Method and Apparatus for Monitoring of Components Housing Wall Thickness and Wear Monitoring," that claims benefit to provisional patent application No. 61/315,233, filed 18 Mar. 2010, which are both incorporated herein by reference in their entirety. See also the corresponding U.S. national stage patent application Ser. No. 13/635,449, filed 17 Sep. 2012, which is also incorporated herein by reference in its entirety.

Such NDE approaches may, however, not be highly effective for the detection of the thickness of coating on the interior of the pipe due to the poor impedance discrimination of the liner or lining and fluid material (as compared to a pipe wall—often steel—and the fluid, where the pipe does not have a liner). Consequently, monitoring the status of a lined pipe may be a challenge, and catastrophic failure can result if an incorporated lining is damaged and tears away from the outer steel pipe, exposing it directly to the fluid abrasion/corrosion, or if scale build-up rapidly escalates to block the pipe.

Further, another problem in the art relates to the need to overcome the significant wear that can occur in pipelines carrying slurry materials, particularly as in the oil sands industry, many suppliers are adopting 'lined' pipes, including where materials, such as urethanes and other elastomers, may be used. A good example is Irathance from a company named Iracore. These materials provide good resistance to abrasion, but ultrasonic NDE approaches for detecting the lining thickness are typically not effective due to the poor impedance discrimination of the lining and slurry material (as compared to a steel pipe wall (without a liner) and the slurry). Consequently, monitoring the status of a lined pipe can also be a challenge.

In view of this, there is a need in the industry to provide a better way for determining coating wear, or scale build-up, or liner wear.

SUMMARY OF THE INVENTION

In its broadest sense, the present invention provides apparatus that includes, or takes the form of, a signal processor configured to receive signaling containing information about an acoustic signal swept and sensed over a frequency range in relation to a pipe; and determine information about the structure of the pipe based at least partly on two or more sub-frequency ranges that form part of the frequency range in the signaling received. This apparatus can be used to perform an acoustic probing technique for the determination of interior pipe coating wear, or scale build-up, or liner wear.

Determination of Interior Pipe Coating Wear or Scale Build-Up

According to some embodiments of the present invention, the signal processor may be configured to receive the acoustic signal being transmitted to the pipe and corresponding signaling in the two or more sub-frequency ranges containing information about reflections of the acoustic signal back from the pipe; and determine information about the structure of the pipe based at least partly on a coherent mixing of the acoustic signal and the corresponding signaling in the two or more sub-frequency ranges using a coherent acoustic tomography technique.

For example, this technique allows various components of a wall of the pipe to be assesses, including incorporated coatings, or undesirable scale/deposit build up. The approach is termed "Coherent Acoustic Tomography (CAT)." In CAT, the structure of the pipe wall may be assessed using a continuous frequency swept acoustic probe approach, in which the acoustic (ultrasonic) signals reflected/scattered from different layers in the pipe wall may be coherently mixed with a signal directly the acoustic transmitter. The transit path difference encountered by the ultrasound signal returned from each scattering layer may then be encoded onto a different beat signal. A Fast Fourier Transformation (FFT) of the output then may be used to transpose the depth of the scattering into frequency and the amplitude as the scattering/reflection coefficient.

For example, in the case of the build up of scale on the interior of a steel pipe, as the scale builds, it adds thickness to the pipe wall, but the acoustic properties are not uniform across the pipe-to-scale layer. The different acoustic properties of the scale material result in a discrete reflection from the interface between the pipe wall material (e.g., steel) and the scale deposits result in weak acoustic scattering and a weak 'discrete' reflection from the scale-to-fluid interface. In normal ultrasonic NDE type analysis, the reflections from the scale-to-fluid layer will typically be weak, as generally the acoustic impedance mismatch is not high enough, and the scale surface may not be uniform. In contrast, the coherent detection nature of the approach described herein according to the present invention may be configured to provide an improved way or ability to detect weakly reflecting surfaces and regions inside the pipe wall.

In operation, an ultrasonic acoustic beam may be coupled from an ultrasonic transmitter unit, Tx, into the wall of the pipe. Reflections may arise from:
  1) A main pipe wall interior interface/boundary layer,
  2) A scattering due to imperfections/voids in secondary coating,
  3) Final interior face of secondary coating.

Mixing of received reflection signals with the drive ultrasonic signal produces a beat signal proportional to the transit delay in the sensing path. An FFT of the output may be used to translate the frequency content into the spatial domain, and sections/coatings of the pipe can be identified by the various peaks in the transformation.

Some advantages of the present invention may be attributed to the fact that the apparatus or system encodes the depth/distance into a frequency. It also has the potential to allow scattering from an imperfect coating (e.g. w/voids etc.) to be detected. Weak reflectors on the time domain still show as resolvable peaks in frequency The are example of frequencies that may be used:
  A 1-3 MHz scan at 1 kHz rep rate (ramp)-2 MHz sweep in 1000 uS.
  A Tx-Rx reflection delay in pipe wall (say 20 mm steel) corresponds to ~10 uS
  A beat frequency=(2 MHz×10 uS/1000 uS)=20 kHz . . . 1 kHz per mm thickness Determination of Liner Wear Alternatively, according to some embodiment of the present invention, the signal processor may be configured to receive associated signaling in the two or more sub-frequency ranges containing information about associated resonance in a liner of a wall of the pipe and determine information about the liner of the wall of the pipe, based at least partly on the two or more sub-frequency ranges. For example, in this technique miniature acoustic resonators, resonant at different frequencies, are embedded into the lining or liner of a wear-resistant pipe to allow the indication of wear rate of the liner through external acoustic probing of the pipe via acoustic and preferentially ultrasonic excitation. In operation, as the liner is abraded, one or more of the small acoustic resonators may be destroyed and the associated resonance may no longer detected externally, thus indicating the wear in the liner material. The approach can be used at a single depth in the liner, or at multiple depth using different acoustic resonator frequency to indicated wear rate and give an ability to predict pipe lifetime.

The Method

Further, the present invention may also take the form of a method comprising steps of: receiving in a signal processor signaling containing information about an acoustic signal swept and sensed over a frequency range in relation to a pipe; and determining in the signal processor information about the structure of the pipe based at least partly on two or more sub-frequency ranges that form part of the frequency range in the signaling received.

According to some embodiment of the present invention, the method may further comprise: receiving in the signal processor the acoustic signal being transmitted to the pipe and corresponding signaling in the two or more sub-frequency ranges containing information about reflections of the acoustic signal back from the pipe; and determining in the signal processor information about the structure of the pipe based at least partly on a coherent mixing of the acoustic signal and the corresponding signaling in the two or more sub-frequency ranges using a coherent acoustic tomography technique.

Alternatively, according to some embodiment of the present invention, the method further comprises: receiving in the signal processor associated signaling in the two or more sub-frequency ranges containing information about associated resonance in a liner of a wall of the pipe; and determining in the signal processor information about the liner of the wall of the pipe wall, based at least partly on the two or more sub-frequency ranges.

The method according to the present invention may include one or more of the aforementioned features, as well.

Overall, the present invention provides a better way for determining coating wear or scale build-up and liner wear and satisfies a need in the industry, including the oil and gas industry.

BRIEF DESCRIPTION OF THE DRAWING

The drawing includes FIGS. 1-5, which are not necessarily drawn to scale, as follows:

FIG. 1 shows apparatus in the form of a signal processor, according to some embodiments of the present invention.

FIG. 2 shows apparatus for pipe coating thickness monitoring using coherent acoustic tomography, according to some embodiments of the present invention.

FIG. 3 shows a frequency transfer function representation (amplitude versus frequency) of pipe-wall boundaries due to acoustic scattering and reflection, according to some embodiments of the present invention.

FIG. 4 shows apparatus for an implementing an acoustic probing technique for the determination of pipe liner wear, according to some embodiments of the present invention.

FIG. 5 shows the principles of operation in the form of a combination on the left of a pipe, an ultrasonic transmitter and embedded transmitters in relation to an associated frequency transfer function representation (amplitude versus frequency) on the right, including FIG. 5a having a frequency function showing no liner wear; FIG. 5b having a frequency function showing liner wear to a first indicator; and FIG. 5c having a frequency function showing liner wear to a second indicator, all according to some embodiments of the present invention.

DETAILED DESCRIPTION OF BEST MODE OF THE INVENTION

FIG. 1

FIG. 1 shows apparatus generally indicated as 10 according to some embodiments of the present invention. The apparatus takes the form of a signal processor 10a configured to receive signaling $s_1$ containing information about an acoustic signal swept and sensed over a frequency range in relation to a pipe 20, 40 (see FIGS. 2 and 3); and determine information about the structure of the pipe based at least partly on two or more sub-frequency ranges that form part of the frequency range in the signaling received. By way of example, the frequency range and the two or more sub-frequencies that form part of the frequency range are shown in FIGS. 2-5.

According to some embodiments of the present invention, and consistent with that shown in FIGS. 2-3, the signal processor 10a may be configured to receive the acoustic signal being transmitted to the pipe and corresponding signaling in the two or more sub-frequency ranges containing information about reflections of the acoustic signal back from the pipe; and determine information about the structure of the pipe based at least partly on a coherent mixing of the acoustic signal and the corresponding signaling in the two or more sub-frequency ranges using a coherent acoustic tomography technique. In FIG. 2, the two or more sub-frequencies may include frequencies associated with a pipe wall to interior coating interface peak; frequencies associated with a scattering in a coating; and frequencies associated with an interior pipe coating surface peak, consistent with that disclosed in further detail herein. The coherent acoustic tomography technique may be based at least partly on a continuous frequency swept acoustic probe approach. The coherent acoustic tomography technique may also be based at least partly on a method of producing a three-dimensional image of internal structures of a solid object, including the pipe wall, by sensing differences in the effects on the passage of waves of energy impinging of those structures.

Alternatively, according to some embodiment of the present invention, and consistent with that shown in FIGS. 4-5, the signal processor 10a may be configured to receive associated signaling in the two or more sub-frequency ranges containing information about associated resonance in a liner of a wall of the pipe and determine information about the liner of the wall of the pipe, based at least partly on the two or more sub-frequency ranges. In FIG. 5, the two or more sub-frequencies may include frequencies associated with three embedded resonators, including frequencies associated with no wear shown in FIG. 5a; frequencies associated with wear to a first indicator shown in FIG. 5b; and frequencies associated with wear to a second indicator shown in FIG. 5c, consistent with that disclosed in further detail herein.

The apparatus 10 may also include other modules 10b for implementing the signal processing functionality according to the present invention, including one or more memory modules, busing architecture, input/output modules, etc.

FIGS. 2-3: Determination of Interior Pipe Coating Wear or Scale Build-Up

FIG. 2 shows apparatus 11a that may include one or more of the following: a pipe 20 having a primary pipe wall 22 with a secondary coating 24 that may take the form of a wear resistant coating or a scale buildup; an ultrasonic transmitter (Tx) unit 26; an ultrasonic receiving (Rx) unit 28; a mixer 30; a Fast Fourier Transformation (FFT) module 32; and a 1 to 3 MHz oscillator 34. By way of example, the signal processor 10a may include, or take the form of, some combination of the mixer 30 and/or the FFT module 32 that may be configured to perform the signal processing functionality to implement some embodiments according to the present invention.

For example, in operation, the 1 to 3 MHz oscillator 34 may be configured to respond to, e.g., a low kHz rate sweep signal, and provide the acoustic signal in the form of, e.g., a 1 to 3 MHz oscillator signal. The mixer 30 may be configured to receive the acoustic signal $s_2$ from the 1 to 3 MHz oscillator 34 being transmitted to the pipe 20, and the signaling or corresponding signaling as indicated by reference label $s_1$ from the ultrasonic receiving (Rx) unit 28 in the two or more sub-frequency ranges containing information about reflections of the acoustic signal back from the pipe 20. Moreover, some combination of the mixer 30 and/or the FFT module 32 may be configured to determine information about the structure of the pipe 20 based at least partly on the coherent mixing of the acoustic signal and the corresponding signaling $s_1$ in the two or more sub-frequency ranges using the coherent acoustic tomography technique. The information about the secondary coating 24 may include, e.g., the wear resistant coating or the scale buildup of or on the wall of the pipe 20, although the scope of the invention is intended to include other types or kinds of information about the secondary coating either now known or later developed in the future. The acoustic signal may take the form of an ultrasonic signal, consistent with that disclosed herein. The scope of the invention is also not intended to be limited to using any particular low kHz rate sweep signal or any particular MHz oscillator signal. For example, embodiments are envisioned using other types or kinds of oscillator signals having other oscillation frequencies.

In FIG. 2, the acoustic signal transmitted to the pipe 20, e.g., by the ultrasonic transmitter (Tx) unit 26, causes reflections that are sensed by the ultrasonic receiving (Rx) unit 28, including an interface reflection r1 at the interface between the primary pipe wall 22 and the secondary coating 24, and an interior reflection (plus scattering) r2 back from the interior of the secondary coating 24. In effect, and by way of example, the reflections may arise from some combination of:

1) A main pipe wall interior interface/boundary layer in a first sub-frequency range, or
2) A scattering due to imperfections/voids in the secondary coating in a second sub-frequency range, or
3) A final interior face of the secondary coating in a third sub-frequency range.

The signal processor 10a may be configured to implement the acoustic coherent tomography technique by performing some combination of the following:

Encoding a transit path difference encountered by the acoustic signal returned from each scattering layer onto a different beat signal.

Transposing the depth of the scattering of said each scattering layer into a frequency and the amplitude as a scattering/reflection coefficient, based at least partly on using a Fast Fourier Transformation (FFT).

Mixing received reflection signals with a drive ultrasonic signal and produce a beat signal proportional to a transit delay in a sensing path.

According to some embodiments of the present invention, the signal processor 10a may be configured to provide output signal containing information about the structure of the pipe based at least partly on the two or more sub-frequency ranges, including information about the secondary coating, the interface reflection and the interior reflection.

Ultrasonic transmitter (Tx) units like element 26; ultrasonic receiving (Rx) unit like element 28; mixers like element 30; FFT module like element 32; and 1 to 3 MHz oscillators like element 34 are all known in the art, and the scope of the invention is not intended to be limited to any particular type or kind thereof either now known or later developed in the future.

FIGS. 4-5: Determination of Liner Wear

FIG. 4 shows apparatus 11b that may include one or more of the following: acoustic resonators 40a, 40b, 40c embedded in a lining 42 of a wall of a pipe 44 at a predetermined depth or multiple depths; an external ultrasonic transponder 46 that excited at a range of frequencies (e.g., swept over the frequency range); and a swept ultrasonic source 48. The wear resistance liner or lining 42 may take the form of a lining made of Irathane, although the scope of the invention is intended to include linings made from other type or kinds of material either now known or later developed in the future. By way of example, the acoustic resonators 40a, 40b, 40c may take the form a PVDF strip with a resistor (e.g. an RC circuit), and are configured to resonate at the two or more different sub-frequencies so as to provide the acoustic signal to be sensed by the external ultrasonic transponder 46. The external ultrasonic transponder 46 is configured to receive a swept ultrasonic source signal from the swept ultrasonic source 48, and to be "tuned in" to the two or more different sub-frequencies of the acoustic signal at which the acoustic resonators 40a, 40b, 40c are resonating and to detect the two or more different sub-frequencies of the acoustic signal by absorption, which is an effective energy transfer technique. In operation, the signal processor 10a may be configured to receive the associated signaling containing information about the acoustic signal swept and sensed by the external ultrasonic transponder 46 over the frequency range in relation to the pipe 44; and determine information about the liner or lining 42 of the wall of pipe 44 based at least partly on two or more sub-frequency ranges that form part of the frequency range in the associated signaling received. FIG. 5 shows frequencies associated with no wear shown in FIG. 5a; frequencies associated with wear to the first indicator shown in FIG. 5b; and frequencies associated with wear to the second indicator shown in FIG. 5c.

According to some embodiments of the present invention, the signal processor 10a may be configured to provide output signaling containing information, e.g., including that one or more acoustic resonators like elements 40a, 40b, 40c may be destroyed and the associated resonance may no longer detected externally, thus indicating the wear in the liner material, as the liner 42 is abraded.

Acoustic resonators like elements 40a, 40b, 40c, external ultrasonic transponders like element 46 and swept ultrasonic sources like elements 48 are all known in the art, and the scope of the invention is not intended to be limited to any particular type or kind thereof either now known or later developed in the future.

The Signal Processor 10a

By way of example, and consistent with that described herein, the functionality of the signal processor 10a may be implemented using hardware, software, firmware, or a combination thereof, although the scope of the invention is not intended to be limited to any particular embodiment thereof. In a typical software implementation, the signal processor 10a would be one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality described herein without undue experimentation. The scope of the invention is not intended to be limited to any particular implementation using technology now known or later developed in the future. Moreover, the scope of the invention is intended to include the signal processor 10a being a stand alone module, as shown, or in the combination with other circuitry for implementing another module. Moreover, the real-time part may be implemented in hardware, while non real-time part may be done in software.

The apparatus 10 is also understood to include one or more other modules 10b for implementing the signal processing functionality, including one or more memory modules, busing architecture, and/or input/output modules.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:
1. Apparatus comprising:
a signal processor configured to
receive signaling containing information about an acoustic signal swept and sensed over a frequency range having sub-frequency ranges in relation to a pipe having an inside wall with an interior coating or liner arranged thereon; and
determine further signaling containing information about the interior coating or liner of the pipe using an acoustic probing technique based upon the sub-frequency ranges sensed in the signaling received.
2. Apparatus comprising:
a signal processor configured to
receive signaling containing information about an acoustic signal transmitted, swept and sensed over a frequency range in relation to a pipe and corresponding signaling in two or more sub-frequency ranges that form part of the frequency range containing information about reflections of the acoustic signal back from the pipe; and
determine further signaling containing information about the structure of the pipe based at least partly on a coherent mixing of the acoustic signal and the corresponding signaling in the two or more sub-frequency ranges using a coherent acoustic tomography technique.
3. Apparatus according to claim 2, wherein the signal processor is configured to encode a transit path difference encountered by the acoustic signal returned from each scattering layer onto a different beat signal.

4. Apparatus according to claim 3, wherein the signal processor is configured to transpose the depth of the scattering of said each scattering layer into a frequency and the amplitude as a scattering/reflection coefficient, based at least partly on using a Fast Fourier Transformation (FFT).

5. Apparatus according to claim 2, wherein the reflections arise from:
   1) A pipe wall interior interface/boundary layer in a first sub-frequency range, or
   2) A scattering due to imperfections/voids in a secondary coating in a second sub-frequency range, or
   3) A final interior face of the secondary coating in a third sub-frequency range, or
   4) Some combination thereof.

6. Apparatus according to claim 2, wherein the signal processor is configured to the mix received reflection signals with a drive ultrasonic signal and produce a beat signal proportional to a transit delay in a sensing path.

7. Apparatus according to claim 2, wherein the apparatus comprises an ultrasonic transmitter unit configured to be arranged in relation to a wall of the pipe and to provide an ultrasonic signal to the pipe wall.

8. Apparatus according to claim 2, wherein the apparatus comprises an ultrasonic receiver unit configured to be arranged in relation to a wall of the pipe and to provide the corresponding signaling to the signal processor.

9. Apparatus according to claim 2, wherein the information determined allows various components of a wall of the pipe to be assesses, including incorporated coatings, or undesirable scale/deposit build up.

10. Apparatus according to claim 2, wherein the continuous frequency swept acoustic probe approach includes using one or more of the following:
   1-3 MHz scan at 1 kHz repetition rate (ramp), including a 2 MHz sweep in 1000 uS, or
   a Tx-Rx reflection delay in a wall of the pipe, including where the Tx-Rx reflection delay for a 20 mm steel pipe wall corresponds to about 10 uS, or
   a beat frequency that equals about 20 kHz, including where the beat frequency is about 1 kHz per mm thickness.

11. Apparatus according to claim 2, wherein the coherent acoustic tomography technique is based at least partly on a continuous frequency swept acoustic probe approach.

12. Apparatus according to claim 2, wherein the coherent acoustic tomography technique is based at least partly on a method of producing a three-dimensional image of internal structures of a solid object, including the pipe wall, by sensing differences in the effects on the passage of waves of energy impinging of those structures.

13. Apparatus according to claim 2, wherein the signal processor is configured to provide output signaling containing information about the structure of the pipe based at least partly on two or more sub-frequency ranges, including information about a secondary coating, an interface reflection and an interior reflection.

14. Apparatus according to claim 13, wherein the secondary coating includes a wear resistant coating or a scale build up.

15. Apparatus comprising:
a signal processor is configured to
    receive signaling containing information about an acoustic signal swept and sensed over a frequency range having sub-frequency ranges in relation to a pipe having an inside wall with an interior liner, and associated signaling in the sub-frequency ranges containing information about associated resonance sensed in the interior liner of the pipe; and
    determine further signaling containing information about the wear of the interior liner of the pipe, based at least partly on the presence or absence of the associated resonance sensed in the sub-frequency ranges in the associated signaling received.

16. Apparatus according to claim 15, wherein the apparatus comprises at least one acoustic resonator embedded in the interior liner of the inside wall of the pipe at a predetermined depth or at multiple depths configured to sense the associated resonance, and provide acoustic resonator signaling containing information about the associated resonance sensed.

17. Apparatus according to claim 15, wherein the signal processor is configured to receive the associated signaling from a transponder containing information about acoustic signals from two or more acoustic resonators, resonant at different frequencies, that are embedded into the interior liner of the inside wall of the pipe to allow the indication of wear rate of the interior liner through external acoustic probing of the pipe via acoustic excitation, including ultrasonic excitation.

18. Apparatus according to claim 17, wherein the apparatus comprises some combination of the transponder and the two or more acoustic resonators.

19. Apparatus according to claim 18, wherein the two or more acoustic resonators are configured in the interior liner at a single predetermined depth, or at multiple depths using different acoustic resonator frequencies to indicated wear rate, including providing an ability to predict pipe lifetime.

20. Apparatus according to claim 19, wherein the signal processor is configured to provide output signaling containing information that one or more acoustic resonators is destroyed and the associated resonance is no longer detected externally, thus indicating the wear in the liner material, as the interior liner is abraded.

21. Apparatus according to claim 18, wherein the two or more acoustic resonators are configured with a PVDF strip with a resistor, including a resistor/capacitor circuit.

22. Apparatus according to claim 17, wherein the apparatus comprises an external acoustic transponder, including an ultrasonic transponder, configured to excite in respond to the acoustic signals in the frequency range.

23. Apparatus according to claim 17, wherein the apparatus comprises the external acoustic transponder is configured to be "tuned in" the two or more sub-frequency so as to detect the two or more acoustic resonators, based at least partly on energy absorption so as to use an effective energy transfer mechanism.

* * * * *